United States Patent [19]

Brown et al.

[11] Patent Number: 4,826,817

[45] Date of Patent: May 2, 1989

[54] AMINO ACID AND HYDROXYAMINO ACID TRANSPORTER COMPOUNDS FOR THERAPEUTIC APPLICATIONS, PROCESS AND USE

[76] Inventors: Thomas E. Brown, 49 Alan Rd., Spring Valley, N.Y. 10977; Thomas P. Brown, 2930 N. 52nd St., No. 308, Phoenix, Ariz. 85018; Thomas A. Ban, 2304 Valley Brook Rd., Nashville, Tenn. 37215

[21] Appl. No.: 827,992

[22] Filed: Feb. 7, 1986

[51] Int. Cl.$^4$ ............................................. A61K 37/02
[52] U.S. Cl. ...................................................... 514/19
[58] Field of Search ........................................... 514/19

[56] References Cited

U.S. PATENT DOCUMENTS 4,503,040  3/1985  Barth ................................... 424/114

OTHER PUBLICATIONS

Chem. Abstr. vol. 104, (1986), 39716.
Chem. Abstr. vol. 103, (1985), 105272.
Chem. Abstr. vol. 102, (1985), 221198.
Drug Design Fact or Fantasy, (1984), p. 53.

Primary Examiner—Phillips Delbert R.
Attorney, Agent, or Firm—Ostrolenk, Faber, Gerb & Soffen

[57] ABSTRACT

Amino acid and hydroxyamino acid transporter compounds are provided, in which an amino acid or hydroxyamino acid as a carrier is linked via an ester linkage to a therapeutic compound, and having one of the general formulae:

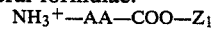

$$NH_3{}^+ - AA - COO - Z_1 \qquad\qquad I$$

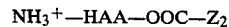

$$NH_3{}^+ - HAA - OOC - Z_2 \qquad\qquad II$$

in which AA represents the amino acid or hydroxyamino acid, HAA represents the hydroxyamino acid, and $Z_1$ and $Z_2$ represent a therapeutic compound, or a linking compound attached to COOH or OH of the hydroxyamino acid and to the therapeutic compound, as well as a process for preparing the same, and a process for administration of the same to animals, to obtain the benefit of the therapeutic effect of the therapeutic compound.

14 Claims, No Drawings

AMINO ACID AND HYDROXYAMINO ACID TRANSPORTER COMPOUNDS FOR THERAPEUTIC APPLICATIONS, PROCESS AND USE

Disorders in animals including man are treated by administration of a therapeutic agent, whose therapeutic effect is obtained only upon absorption and utilization in the metabolic system of the animal. If the therapeutic agent cannot be absorbed readily in the metabolic system, its capabilities and effectiveness naturally are greatly diminished.

A prerequisite for absorbability of a therapeutic agent is that it penetrate biological barriers, such as the blood brain barrier or cell membranes. The ability of a therapeutic agent to penetrate such barriers is greatly influenced by the chemical and physical properties of the agent, and also upon the integrity and chemical nature of the barrier or membrane.

In general, hydrophilic therapeutic agents are readily absorbed and lipophilic therapeutic agents are poorly absorbed by the animal body. Lipophilic therapeutic agents penetrate biological membranes at slow rates of transport, generally by passive mechanisms, in part because active transport mechanisms across biological membranes and similar barriers exist only for hydrophilic compounds. Therapeutic compounds having a high molecular weight and/or a complex spatial arrangement of the molecule, often features of pharmacologically active compounds because spatial structure is frequently most important in therapeutic activity, also are transported only slowly across biological membranes.

Traditionally, research efforts to improve transport have endeavoured to manipulate the molecule of the therapeutic agent by adding groups that enhance solubility and therefore bioavailability of the compound. Such an approach has several inherent disadvantages. First, a new compound is created, of uncertain therapeutic effectiveness. Since the compound is new, existing regulatory requirements require a complete and costly reevaluation of the new compound's effectiveness and toxicity, including carcinogenic potential, and this is of course involves considerable expense and effort, as well as time, and may be unsuccessful. Completion of the reevaluation may only show that the compound has a substantially different therapeutic effectiveness in animals, because of the altered structure/activity relationship. In many instances, toxicity problems arise. Such new compounds may be carcinogenic, even though the predecessor molecule is not.

In accordance with the present invention, a new approach is made utilizing an amino acid or hydroxyamino acid as a transporter for known therapeutic agents, linking the amino acid or hydroxyamino acid to the therapeutic agent by way of an ester linkage between the amino acid or hydroxyamino acid molecule and the molecule of the therapeutic agent. A preferred amino acid is lysine, having two amino groups with a positive charge and a considerable hydrophilic character, and a preferred hydroxyamino acid is serine. The amino acid or hydroxyamino acid acts as a carrier for the therapeutic compound, in transport of the compound across biological barriers, including cell membranes and the blood brain barrier. After passage of the barrier, the new compound enters the metabolic system of the animal, where the ester linkage is destroyed by naturally-occurring esterases present in the animal, thus regenerating free amino acid or hydroxyamino acid and the known therapeutic compound. Since the known therapeutic compound is of known therapeutic effectiveness, no problems with existing regulatory requirements arise. Similarly, since amino acids and hydroxyamino acids as a class, including in particular lysine and serine, are known to be safe and nontoxic, no problems arise because of its presence. The result is a considerably enhanced capability of the therapeutic agent to be absorbed in the metabolic system of the animal, without any complicating side effects.

The amino acid and hydroxyamino acid transporter compounds in accordance with the invention can link to the therapeutic compound via a carboxylic acid group COOH of the amino acid or hydroxyamino acid, or via a hydroxyl group of the hydroxyamino acid, and accordingly have one of the following general formulae:

$$NH_3^+\text{—AA—COO—Z} \qquad \text{I}$$

(linked via a COOH group of the amino acid or hydroxyamino acid)

$$NH_3^+\text{—HAA—OOC—Z} \qquad \text{II}$$

(linked via a hydroxyl group of the hydroxyamino acid)

In the above formulae, AA represents the amino acid or hydroxyamino acid, HAA represents the hydroxyamino acid, radical linked to COO— or O—; Z represents (1) therapeutic compound, or (2) a therapeutic compound and a linking compound attached to the COOH or OH of the amino acid or hydroxyamino acid, and via another ester group to the therapeutic compound.

Any therapeutic compound having a hydroxyl, carboxylic acid or acyl group can form an ester linkage with (a) the amino acid or hydroxyamino acid directly, by way of a carboxy group of the amino or hydroxyamino acid, or (b) a linking compound having a carboxyl group, in the case of a hydroxyl group on the therapeutic compound, or with (c) a hydroxyl group on the hydroxyamino acid, or (d) a hydroxyl group on the linking compound, with a carboxylic or acyl group on the therapeutic compound.

The linking compound provides a way of forming the ester linkage with the amino or hydroxyamino acid of a therapeutic compound with a carboxylic acid or acyl group, since the linking compound can have two hydroxyl groups, or one hydroxyl and one acid group, which can form easter linkages, one with carobxylic acid group of the amino or hydroxyamino acid, and one with the carboxylic acid or acyl or hydroxyl group of the therapeutic compound. These compounds constitute a subclass within Formula I that have one of the general formulae:

$$NH_3^+\text{—AA—COO—}Y_1\text{—OOC—}Z_2 \qquad \text{III}$$

$$NH_3^+\text{—AA—COO—}Y_2\text{—COO—}Z_1 \qquad \text{IV}$$

The hydroxyl group of a hydroxyamino acid can also be linked to a carboxylic acid group of a linking compound, which has another carboxylic acid group or one hydroxyl group that can be linked to the hydroxyl or carboxylic acid or acyl group of a therapeutic compound. These compounds constitute a further subclass within formula II that have one of the general formulae:

$$NH_3^+\text{—HAA—OOC—}Y_3\text{—COO—}Z_1 \qquad \text{V}$$

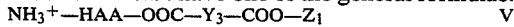

$$NH_3^+\text{—HAA—OOC—}Y_2\text{—OOC—}Z_2 \qquad \text{VI}$$

In the above formulae AA represents an amino acid, HAA represents a hydroxyamino acid, $Z_1$ represents a therapeutic compound having a hydroxy group; and $Z_2$ represents a therapeutic compound having a carboxylic acid or acyl group, $Y_1$ a linking compound having two hydroxyl groups, $Y_2$ a linking compound having one hydroxyl and one carboxylic acid or acyl group, and $Y_3$ a linking compound having two carboxylic acid groups. An example of $Y_1$ is two tyrosine groups linked by a peptide linkage, as in the following example of lysine-tyrosine-linked-tryptophane compounds of Formula VII:

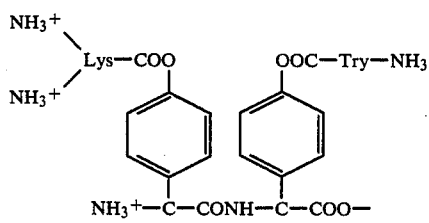
VII

In this example, AA is lysine, Y is a double tyrosine molecule linked by a peptide linkage CONH and Z is tryptophane, linked to Y by way of the carboxylic acid group.

The transporter compounds of the invention can utilize any amino acid, as a class, of which hydroxyamino acids are a preferred subclass. The amino acids have at least one amino group, and at least one carboxylic acid group, and the hydroxyamino acids have at least one amino group, at least one carboxylic acid group and one hydroxyl group. The number of carbon atoms is not critical, except that larger molecules can display diminished solubility in pharmaceutically acceptable solvents; usually the amino acid has from two to about twenty carbon atoms.

A plurality of amino groups and a plurality of carboxylic acid groups and a plurality of hydroxyl groups are no detriment, since all three types of groups are hydrophilic, and thus increase hydrophilicity. The amino acids can have up to five amino groups, up to five carboxylic acid groups, and up to five hydroxyl groups.

The relative positions of the amino, COOH and OH (if any) groups on the molecule are not critical, either, but it is usually preferred that they be α, β, γ or δ to each other, since proximity may be advantageous.

The amino acids and hydroxyamino acids can be aliphatic, cycloaliphatic, mixed aliphatic-aromatic, mixed aliphatic-cycloaliphatic, or mixed cycloaliphatic-aromatic.

Exemplary aliphatic amino acids include: glycine, glycyl glycine, α- and β-alanine, Lysine, tryptophane, valine, norvaline, leucine, isoleucine, norleucine, cystine, methionine, arginine, asparagine, creatine, glutamine, arginine, α-aminobutyric acid, α,ε-diaminopimelic acid, lanthionine, djenkolic acid, γ-methyleneglutamic acid, α, γ-diaminobutyric acid, ornithine, citrulline, and canavarine.

Exemplary cycloaliphatic amino acids include: proline, histidine.

Exemplary mixed aliphatic-aromatic amino acids include: thyroxine, diiodothyroxine and phenylalanine.

Exemplary mixed aliphatic cycloaliphatic amino acids include: histidine.

Exemplary mixed aromatic-cycloaliphatic amino acids include: tryptophane.

Exemplary aliphatic hydroxyamino acids include: hydroxyamino butyric acid, δ-hydroxy lysine, hyroxyvaline tyrosine, serine, threonine, cysteine (with SH instead of OH), aspartic acid, hydroxyglutamic acid, allothreonine, α- and β-thiolvaline, diaminetrihydroxy dodecanoic acid and diaminodihydroxy suberic acid.

Exemplary cycloaliphatic hydroxyamino acids include: hydroxyproline.

Exemplary mixed aliphatic-aromatic hydroxyamino acids include: tyrisine, thyroxine, diiodo tyrosine, and surinamine.

The amino acid and hydroxyamino acid transporter compounds of the present invention are readily prepared by conventional esterification procedures, which are well known in the art. The following Example shows the preparation of O-L-lysyl-L-tyrosine.

Example I

The reaction sequence is shown below:

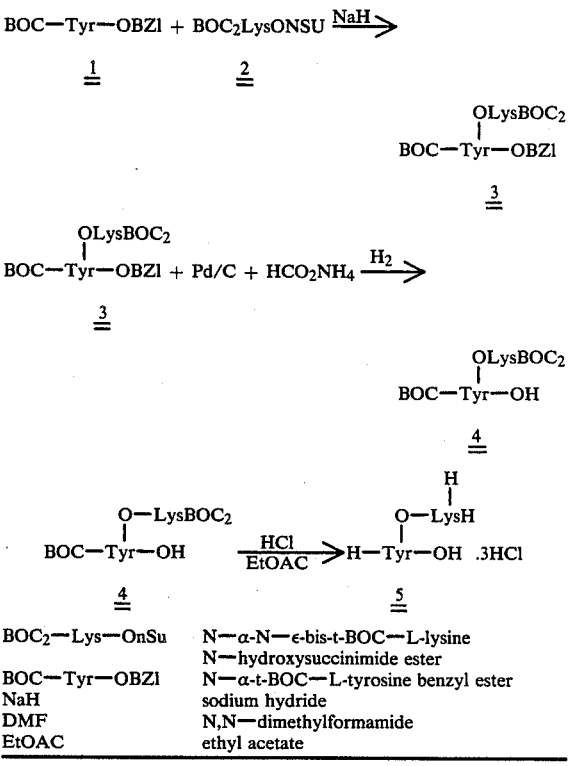

N-α-t-BOC-O-(Nα'-Nε'-bis-t-BOC-L-lysyl)-L-tyrosine benzyl ester[3]

Into a 250 ml 3-neck, round-bottom flask equipped with magnetic stirrer, thermometer, drying tube and cooling bath, were charged 10 g (27.0 mmole) BOC-Tyr-OBZl (1) and 125 ml DMF. The solution was cooled to 0° C., and 1.1 g (27.5 mmole) NaH (60% oil dispersion) was added in one portion. The solution/suspension was stirred one hour at −10°-0° C., then 12.0 g (27.1 mmole) BOC₂LysONSu (2) was added and the reaction stirred overnight at room temperature. The mixture was poured into 250 ml ice/H₂O, then extracted with CH₂Cl₂ (3×350 ml). The combined organic extracts were washed with 1N NaOH (2×500 ml), H$_2$) (3×500 ml), sat. NaCl (1×500 ml) and dried over Na$_2$SO$_4$. The organic phase was then evaporated in vacuo to yield 16.3 g (86%) of a white solid, pure by TLC CHCl$_3$:CH$_2$OH:CH$_2$CO$_2$H-9: 1:1. IR(cm$^{-1}$):3380, 3390(NH); 1700, 1710, 1745, 1768 (c=0). NMR(ppm):2.43 (s, 9H), 2.47 (s, 9H), 2.50 (s, 9H0, 7.03 (M, 4H), 7.34 (M, 5H).

N-α-t-BOC-O-(Nα'-Nε'-bis-t-BOC-L-lysyl0-L-tyrosine 4

Into a 250 ml 3-neck, round-bottom flask equipped with a magnetic stirrer and gas inlet and outlet, were charged 16.1. g3, 90 ml DMF, 4.50 g HCO$_2$NH$_4$ and 4.5 g 10% Pd/c. After scrubbing with N$_2$, H$_2$ was bubbled through the mixture at atmospheric pressure. After 5 minutes, the reduction was complete and the catalyst was filtered off, and the filtrate was partitioned between CH$_2$Cl$_2$/1NHCl (500 ml/500 ml). The organic phase was washed with 1NHCl (1×400 ml), H$_2$O (4×500 ml). saturated NaCl (1×500 ml) and dried over Na$_2$SO$_4$. After evaporation of the CH$_2$Cl$_2$ and trituration with hexane, 13.8 g (97%) of 4 was obtained. TLC: EtOAc:CH$_3$CO$_2$H:hexane-20: 10:1 showed one spot. IR (cm$^{-1}$):3385 (NH); 1675, 1700, 1728, 1770(c=0).

O-L-Lysyl-L-tyrosine-3HCL 5

A solution of 13.5 g (22.2 mmole) 4 in liter EtOAc was placed in a 2 liter, 3 neck, round-bottom flask equipped with magnetic stirrer, gas inlet tube, and drying tube. Anhydrous HCl was bubbled through the solution for 30 minutes. A precipitate appeared after about 15 minutes. The precipitate was filtered off, washed with EtOAc and dried in vacuo to yield 9.3 g (100%) of hygroscopic product. TLC—nBuOH: CH$_2$CO$_2$H: H$_2$O-4: 1: 1 Rf=0.2, trace 0.8. IR(cm$^{-1}$): 1950 (broad NH$_3^+$); 1750, 1700 (c=0).

The invention is broadly applicable to any therapeutic substances having one or more free hydroxyl groups capable of reacting with the carboxylic acid group or groups of the amino or hydroxyamino acid, as in Formula I above, or with one or more free carboxylic acid or acyl groups capable of reacting with the hydroxyl group of α-hydroxyamino acid, as in Formula II above, or of an intermediary linking compound having at least two hydroxyl or carboxylic acid groups, of which one is linked to the amino acid or hydroxyamino acid as in Formulae III, IV, and V above.

The following is a brief list of classes of known therapeutic agents which can be so linked, and whose absorptivity in the metabolic system of animals is thereby greatly facilitated:

(1) amino acids
(2) depsipeptides
(3) peptides
(4) polypeptides
(5) proteins
(6) psychotropic medications known as
    (1) tranquilizers
    (2) sedatives
    (3) antidepressants
    (4) neuroleptics
    (5) hypnotics
    (6) muscle relaxants
    (7) anticonvulsants
    (8) analgesics
    (9) analeptics
    (10) anesthetics
    (11) antiParkinsonian agents
    (12) CNS stimulants
    (13) psychostimulants
(7) antiasthma compounds
(8) antispasmotics
(9) anorexics
(10) cardiovascular agents
    (1) antiarthymics
    (2) antihypertensives
    (3) cardiac glycosides
    (4) antidiuretics
    (5) antimigraines
(11) antibacterials and antiseptics
(12) antibiotics
(13) antineoplastic drugs
(14) anticoagulants
(15) antidiabetic agents
(16) antidiarrheals
(17) antidotes
(18) antifungal agents
(19) antihistamines
(20) antiherpes (and other antiviral)
(21) anti-inflammatory agents
(22) antimetabolites
(23) antimalarials
(24) antiemetics
(25) antiparasitics
(26) antipruiritics
(27) antipyretics
(28) antispasmotics, anticholinergics
(29) biologicals
(30) bronchodilators
(31) calcium preparations
(32) antihyperlipidemics
(33) contraceptives
(34) cough and cold preparations
(35) decongestants
(36) dental preparations
(37) dermatologicals
(38) diagnostics
(39) dietary supplements
(40) hormones
(41) immunosuppressives
(42) ophthalmologicals
(43) parasympatholytics
(44) parasmypathomimetics
(45) prostaglandins The following lysine transporter compounds are exemplary, in which (1) therapeutic compounds are indicated by the symbol "X", where "X" is either 1. vincristine
2. vinblastine
3. methotrexate
4. daunorubicin
5. bleomycin
6. cytosine arabinoside
7. thiotepa
8. dactinomycin
9. doxorubicin
10. mithramycin
11. mitomycin
12. azauridine
13. idoxuridine
14. deoxyuridine
15. paracetemol
16. calicylic acid
17. acetylsalicylic acid
18. lecithin
19. lecithen-peptide-tryptophan 20. cromoglycate
21. doxepin
22. amoxapine
23. thiothixene
24. lorazepam
25. oxazepam
26. temazepam
27. normetazepam
28. leucovorin
29. tyrosine
30. tryptophan
31. dopamine
32. 5-hydroxytryptophan
33. 5-hydroxytryptamine
34. serotonin and in which (2) carrier compounds are indicated by the symbol "R", where "R" is either
1. lysine
2. serine
3. seryllysine
4. lysyllysine
5. lysylserine
6. lysylseryllysine
7. 2,6 diaminohexanol
8. delta hydroxylysine
9. lactic acid
10. 2,4 diamino butanol

EXEMPLARY COMPOUNDS

1. L-R-ester-L-X
2. D-R-ester-L-X
3. D-R-ester-D-X
4. L-R-ester-D-X
5. L-try-ester-L-tyr-peptide-L-tyr-ester-L-R
6. D-try-ester-L-tyr-peptide-L-tyr-ester-L-R
7. L-try-ester-D-tyr-peptide-L-tyr-ester-L-R
8. L-try-ester-L-tyr-peptide-D-tyr-ester-L-R
9. L-try-ester-L-tyr-peptide-L-tyr-ester-D-R
10. D-try-ester-D-tyr-peptide-L-tyr-ester-L-R
11. D-try-ester-L-tyr-peptide-D-tyr-ester-L-R
12. D-try-ester-L-tyr-peptide-L-tyr-ester-D-R
13. L-try-ester-D-tyr-peptide-D-tyr-ester-L-R
14. L-try-ester-D-tyr-peptide-L-tyr-ester-D-R
15. L-try-ester-L-tyr-peptide-D-tyr-ester-D-R
16. D-try-ester-D-tyr-peptide-D-tyr-ester-L-R
17. D-try-ester-D-tyr-peptide-L-tyr-ester-D-R
18. D-try-ester-L-tyr-peptide-D-tyr-ester-D-R
19. L-try-ester-D-tyr-peptide-D-tyr-ester-D-R
20. D-try-ester-D-tyr-peptide-D0tyr-ester-D-R
21. L-R-ester-L-tyr-peptide-L-tyr-ester-L-try
22. D-R-ester-L-tyr-peptide-L-tyr-ester-L-try
23. L-R-ester-D-tyr-peptide-L-tyr-ester-L-try
24. L-R-ester-L-tyr-peptide-D-tyr-ester-L-try
25. L-R-ester-L-tyr-peptide-L-tyr-ester-D-try
26. D-R-ester-D-tyr-peptide-L-tyr-ester-L-try
27. D-R-ester-L-tyr-peptide-D-tyr-ester-L-try
28. D-R-ester-L-tyr-peptide-L-tyr-ester-D-try
29. L-R-ester-D-tyr-peptide-D-tyr-ester-L-try
30. L-R-ester-D-try-peptide-L-tyr-ester-D-try
31. L-R-ester-L-tyr-peptide-D-tyr-ester-D-try
32. D-R-ester-D-tyr-peptide-D-tyr-ester-L-try
33. D-R-ester-D-tyr-peptide-L-tyr-ester-D-try
34. D-R-ester-L-tyr-peptide-D-tyr-ester-D-try
35. L-R-ester-D-tyr-peptide-D-tyr-ester-D-try
36. D-R-ester-D-tyr-peptide-D-tyr-ester-D-try
37. L-try-ester-L-tyr-ester-L-R
38. D-try-ester-L-tyr-ester-L-R
39. L-try-ester-D-tyr-ester-L-R
40. L-try-ester-L-tyr-ester-D-R
41. D-try-ester-D-tyr-ester-L-R
42. D-try-eseter-L-tyr-ester-D-R
43. L-try-ester-D-tyr-ester-D-R
44. D-try-ester-F-tyr-ester-D-R
45. L-R-ester-L-tyr-ester-L-try
46. D-R-ester-L-tyr-ester-L-try
47. L-R-ester-D-tyr-ester-L-try
48. L-R-ester-L-tyr-ester-D-try
49. D-R-ester-D-tyr-ester-L-try
50. D-R-ester-L-tyr-ester-D-try
51. L-R-ester-D-tyr-ester-D-try
52. D-R-ester-D-tyr-ester-D-try
53. L-tyr-ester-L-try-peptide-L-try-ester-L-R
54. D-try-ester-L-try-peptide-L-try-ester-L-R
55. L-tyr-ester-D-try-peptide-L-try-ester-L-R
56. L-tyr-ester-L-try-peptide-D-try-ester-L-R
57. L-tyr-ester-L-try-peptide-L-try-ester-D-R
58. D-tyr-ester-d-try-peptide-L-try-ester-L-R
59. D-tyr-ester-L-try-peptide-D-try-ester-L-R
60. D-tyr-ester-L-try-peptide-L-try-ester-D-R
61. L-tyr-ester-D-try-peptide-D-try-ester-L-R
62. L-tyr-ester-D-try-peptide-L-try-ester-D-R
63. L-tyr-ester-L-try-peptide-D-try-ester-D-R
64. D-tyr-ester-D-try-peptide-D-try-ester-L-R
65. D-tyr-ester-D-try-peptide-L-try-ester-D-R
66. D-tyr-ester-L-try-peptide-D-try-ester-D-R
67. L-tyr-ester-D-try-peptide-D-try-ester-D-R
68. D-tyr-ester-D-try-peptide-D-try-ester-D-R
69. L-R-ester-L-tyr-ester-L-try-peptide-L-try-ester-L-R
70. L-R-ester-D-tyr-ester-L-try-peptide-L-try-ester-L-R
71. L-R-ester-L-tyr-ester-D-try-peptide-L-try-ester-L-R
72. L-R-ester-L-tyr-ester-L-try-peptide-D-try-ester-L-R
73. L-R-ester-L-tyr-ester-L-try-peptide-L-try-ester-D-R
74. L-R-ester-D-tyr-ester-D-try-peptide-L-try-ester-L-R
75. L-R-ester-D-tyr-ester-L-try-peptide-D-try-ester-L-R
76. L-R-ester-D-tyr-ester-L-try-peptide-L-try-ester-D-R
77. L-R-ester-L-tyr-ester-D-try-peptide-D-try-ester-L-R
78. L-R-ester-L-tyr-ester-D-try-peptide-L-try-ester-D-R
79. L-R-ester-L-tyr-ester-L-try-peptide-D-try-ester-D-R
80. L-R-ester-D-tyr-ester-D-try-peptide-D-try-ester-L-R
81. L-R-ester-D-tyr-ester-D-try-peptide-L-try-ester-D-R
82. L-R-ester-D-tyr-ester-L-try-peptide-D-try-ester-D-R
83. L-R-ester-L-tyr-ester-D-try-peptide-D-try-ester-D-R
84. L-R-ester-D-tyr-ester-D-try-peptide-D-try-ester-D-R
85. D-R-ester-L-tyr-ester-L-try-peptide-L-try-ester-L-R
86. D-R-ester-D-tyr-ester-L-try-peptide-ltry-ester-L-R
87. D-R-ester-L-tyr-ester-D-try-peptide-L-try-ester-L-R 88. D-R-ester-L-tyr-ester-L-try-peptide-D-try-ester-L-R
89. D-R-ester-L-tyr-ester-L-try-peptide-L-try-ester-D-R
90. D-R-ester-D-tyr-ester-D-try-peptide-L-try-ester-L-R
91. D-R-ester-D-tyr-ester-L-try-peptide-D-try-ester-L-R
92. D-R-ester-D-tyr-ester-L-try-peptide-L-try-ester-D-R
93. D-R-ester-L-tyr-ester-D-try-peptide-D-try-ester-L-R
94. D-R-ester-L-tyr-ester-D-try-peptide-L-try-ester-D-R
95. D-R-ester-L-tyr-ester-L-try-peptide-D-try-ester-D-R
96. D-R-ester-D-tyr-ester-D-try-peptide-D-try-ester-L-R
97. D-R-ester-D-tyr-ester-D-try-peptide-L-try-ester-D-R
98. D-R-ester-D-tyr-ester-L-try-peptide-D-try-ester-D.R
99. D-R-ester-L-tyr-ester-D-try-peptide-D-try-ester-D-R
100. D-R-ester-D-tyr-ester-D-try-peptide-D-try-ester-D-R The amino acid and hydroxy amino acid transporter compounds in accordance with the invention can be administered to animals as a class, including man, and both large and small animals, by any conventional administration procedure applicable to lysine itself, including, for example, oral administration, transdermal administration, transnasal administration, inhalation, sublingual administration, rectal administration and parenteral administration. The compounds can be administered as such or with a nontoxic inert therapeutic carrier.

The amino acid and hydroxyamino acid transport compound can be administered per se, or in association with a pharmaceutically acceptable diluent or carrier. The invention accordingly also provides a pharmaceutical composition in dosage unit form comprising from 0.1 to about 500 mg of amino acid and hydroxyamino acid transporter compound, per dosage unit, together with a pharmaceutically acceptable nontoxic inert carrier or diluent therefor.

The amino acid and hydroxyamino acid transporter compound can be administered to the animal in an amount to provide therapeutic compound in an amount sufficient to ameliorate the condition alleviated by the therapeutic compound, and will depend upon the condition, the species of animal, and the weight of the animal. For example, in human administration, a dosage of amino acid and hydroxyamino acid transporter compound within the range from about 0.1 mg/kg to about 500 mg/kg per day. In the treatment of lower test animals, a similar dosage range is therapeutic. The upper limit of dosage is that imposed by toxic side effects, and can be determined by trial and error for the animal to be treated, including humans.

To facilitate administration, the amino acid and hydroxyamino acid transporter compound can be provided in composition form, and preferably in dosage unit form. While the compound can be administered per se, it is normally administered in conjunction with a pharmaceutically acceptable carrier thereof, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the lysine transporter compound. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl- and propylhydroxybenzoate, talc or magnesium stearate.

For convenience in handling, the amino acid and hydroxyamino acid transporter compound and carrier or diluent can be enclosed or encapsulated in a capsule, sachet, cachet, gelatin, paper or other container, especially when intended for use in dosage unit. The dosage units can for example take the form of tablets, capsules, suppositories or cachets.

The following Examples illustrate various forms of dosage units in which the amino acid and hydroxyamino acid transporter compound can be prepared:

| Tablet formulation | Mg/tablet |
|---|---|
| Amino acid and hydroxyamino acid transporter compound | 15 |
| Lactose | 86 |
| Corn starch (dried) | 45.5 |
| Gelatin | 2.5 |
| Magnesium stearate | 1.0 |

The amino acid and hydroxyamino acid transporter compound is powered and passed through a mesh sieve and well mixed with the lactose and 30 mg of the corn starch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

| Tablet formulation | Mg/tablet |
|---|---|
| Amino acid and hydroxyamino acid transporter compound | 100 |
| Lactose | 39 |
| Corn starch (dried) | 80 |
| Gelatin | 4.0 |
| Magnesium stearate | 2.0 |

The method of preparation is identical with that of Example 1 except that 60 mg of starch is used in the granulation process and 20 mg during tabletting.

| Capsule formulation | Mg/capsule |
|---|---|
| Amino acid and hydroxyamino acid transporter compound | 250 |
| Lactose | 150 |

The amino acid and hydroxyamino acid transporter compound and lactose are passed through a sieve and the powders well mixed together before filling into hard gelatin capsules of suitable size, so that each capsule contains 400 mg of mixed powders.

| Suppositories | Mg/suppositories |
|---|---|
| Amino acid and hydroxyamino acid transporter compound | 50 |
| Oil of Theobroma | 950 |

The amino acid and hydroxyamino acid transporter compound is powdered and passed through a sieve and triturated with molten oil of theobroma at 45° C. to form a smooth suspension.

The mixture is well stirred and poured into molds, each of nominal 1 g capacity, to produce suppositories.

| Cachets | Mg/cachet |
|---|---|
| Amino acid and hydroxyamino acid transporter compound | 100 |
| Lactose | 400 |

The amino acid and hydroxyamino acid transporter compound is passed through a mesh sieve, mixed with lactose previously sieved and fitted into cachets of suitable size so that each contains 500 mg.

| Intramuscular injection (sterile suspension in aqueous vehicle) | Mg |
|---|---|
| Amino acid and hydroxyamino acid transporter compound | 10 |
| Sodium citrate | 5.7 |
| Sodium carboxymethylcellulose | 2.0 |
| Methyl para-hydroxybenzoate | 1.5 |
| Propyl para-hydroxybenzoate | 0.2 |
| Water for injection to 1.0 ml | |

| Intraperitoneal intraveneous or subcutaneous injection (sterile solution in aqueous carrier system) | Mg |
|---|---|
| Amino acid and hydroxyamino acid transporter compound | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

Following administration of the amino acid and hydroxyamino acid transporter compound, the metabolic system of animal, utilizing the activity of esterases naturally present, will cleave the ester bond linking the amino acid and hydroxyamino acid to the therapeutic compound, and therefore make it available to exert its therapeutic effect in the animal body. The therapeutic effectiveness of the compounds following administration has been demonstrated by laboratory tests in small animals, as is evidenced by the following Example.

EXAMPLE 1

In this Example, the compound O-L-lysyl-L-tyrosine was employed as the test compound.

Male CD-COBS rats (Charles River, Italy) weighing 200 g were used. The animals housed under standard conditions of light-dark cycle, temperature and humidity with free access to water and food. O-L-lysyl-L-tyrosine was dissolved in saline and injected intraperitoneally (i.p.) and intravenously (i.v.) 2 ml/kg at the equimolar dose of 1.62 mmol/kg. L-tyrosine was suspended in 0.5% carboxymethylcellulose and injected only i.p. (because it is insoluble in aqueous solvent) at the equimolar dose of 1.62 mmol/kg. Controls received saline. Rates were killed by decapitation 30 and 120 min. after treatment. Plasma and brain were rapidly removed and kept at $-20°$ C. until assay. L-tyrosine was assayed by electrochemical detection coupled with HPLC according to Holman et al. (R. B. Holman and B. M. Snage, 1983, *J. Chromatogr.* 262, 415–419) with minor modifications.

As shown in Table I, brain L-tyrosine concentrations were significantly increased by O-L-lysyl-L-tyrosine at both intervals considered. Plasma L-tyrosine was significantly raised by only 30 min. after the i.v. dose. As shown in Table II, brain L-tyrosine concentrations were significantly increased after i.p. doses of L-tyrosine ($p<0.05$) and O-L-lysyl-L-tyrosine ($p<0.01$) at both intervals considered. Plasma L-tyrosine was raised only after O-L-lysyl-L-tyrosine and only 30 min. after injection.

TABLE I

Plasma and brain levels of L—tyrosine after intravenous injection of O—L—lysyl-L—tyrosine (1.62 mmol/kg) to rats

| | | Tyrosine ($\mu$g/g ± S.E.) | |
|---|---|---|---|
| Compound | Time (min) | Plasma | Brain |
| Saline | 0 | 11.21 ± 0.95 | 13.21 ± 0.63 |
| Lys-tyrosine | 30 | 46.80 ± 2.99[1] | 49.02 ± 1.50[1] |
| Lys-tyrosine | 120 | 16.50 ± 4.01 | 31.57 ± 0.70˙ |

[1]$p<0.01$ Dunnett's test
Data are the mean of five animals.

TABLE II

Plasma and brain levels of L-tyrosine after intraperitoneal injection of equimolar doses of 1.62 mmol/kg of L-tyrosine and O—L-iysyl-L—tyrosine to rats

| | | L-tyrosine ($\mu$g/g ± S.E.) | |
|---|---|---|---|
| Compound | Time (min) | Plasma | Brain |
| Saline | — | 11.27 ± 1.85 | 13.68 ± 0.83 |
| L-tyrosine | 30 | 16.92 ± 2.06 | 20.22 ± 1.75[1] |
| L-tyrosine | 120 | 12.72 ± 2.23 | 21.77 ± 1.52[1] |
| Lys-tryosine | 30 | 26.48 ± 1.64[2+] | 54.04 ± 3.78[2++] |
| Lys-tyrosine | 120 | 14.59 ± 1.87 | 40.68 ± 2.21[++] |

[1]$p < 0.05$  
[2]$p < 0.01$ } Dunnett's test (vs controls)

+$p < 0.05$  
++$p < 0.01$ } Tukey's test (vs L—tyrosine 30')

$p < 0.01$ Tukey's test (vs L—tyrosine 120')
Data are the mean of four animals.

The transporter compound of the invention that is composed of lysine and tryptophan linked by an ester linkage is of particular therapeutic interest because it is a combination of two natural amino acids. Tryptophan is one of the twenty-two amino acids of animal protein, and normally about 7 mg per kilogram of body weight is required in the daily diet. It is a precursor to serine, one of the neurotransmitters, and is found in man mainly in the intestines, platelets, and the brain. Serine is believed to have a role in certain mental disorders, including endogenous and psychotic depression.

Tryptophan is hydrophobic because of the influence of its side chain. This hydrophobicity is overcome by the linkage with lysine, which is hydrophilic.

Lysine is another essential amino acid of interest, because its basic side chain $NH_3^+$ often imparts a positive electrical charge to the protein into which it has been incorporated, and also enhances its solubility in water. Therefore, coupling with tryptophan has profound effects upon the bioavailability and therefore the clinical uses of the combination in animal applications.

Tryptophan is used empirically in many parts of the world as a hypnotic, as a mild tranquilizer, and even as an antidepressant, either as a single agent or in combination with other antidepressants and neuroleptics. Accordingly, the lysine-tryptophan compounds of the invention, when used in combination with other drugs, can permit a substantial lowering of the effect dose of the other drug, with fewer dose-related adverse reactions. This new safety margin with psychtropic sparing action can be particularly useful with neuroleptic agents.

The enhanced bioavailability of tryptophan in the lysinetryptophan compounds of the invention make it useful as a hypnotic, sedative, muscle relaxant, and antidepressant. There is no evidence to indicate interaction between tryptophan and alcohol, indicating that the compound can be administered safely to people who consume alcohol. The compound can also be useful to dampen distortions of the biological clock, with few, if any, side effects. The compound can also be administered to animals for the treatment of neurotic disorders, distress, pain and anxiety, such as during travel.

In the claims, the term "amino acid" is used generically to encompass all amino acids having at least one amino and one carboxylic acid group including hydroxyamino acids that in addition have at least one hydroxyl group.

Having regard to the foregoing disclosure the following is claimed as the inventive and patentable embodiments thereof:

1. An amino acid transporter compound in which amino acid as a carrier is linked via an hydrolyzably ester linkage to a therapeutic compound and having the formula:

$$NH_3^+-AA-COO-Z_1 \quad\quad I$$

in which AA is lysine $Z_1$ is a therapeutic compound linked via a hydroxyl group thereof to a carboxylic acid group of the amino acid or a linking compound attached to —COO— of the amino acid and to the therapeutic compound.

2. An amino acid transporter compound according to claim 1 in which $Z_1$ is tryptophane.

3. An amino acid transporter compound according to claim 1 having the formula:

$$NH_3^+-AA-COO-Y_1-OOC-Z_2 \quad\quad III$$

$$NH_3^+-AA-COO-Y_2-COO-Z_1 \quad\quad IV$$

in which hydrolyzably $Y_1$ is a linking compound having two hydroxyl groups and $Y_2$ is a linking compound having one hydroxyl and one carboxylic acid or acyl group.

4. An amino acid transporter compound according to claim 3 in which Y is a tyrisine-peptide-tyrosine group.

5. An amino acid transporter compound according to claim 4 in which $Z_1$ and $Z_2$ are tryptophane.

6. A pharmaceutical composition in dosage unit form for treating a condition for which the therapeutic compound is effective, comprising an amount within the range from about 0.1 to about 500 mg of an amino acid transporter compound according to claim 1 per dosage amount therapeutically effective to ameliorate the condition for which the therapeutic compound is effective, together with a pharmaceutically acceptable nontoxic carrier or diluent therefor.

7. A pharmaceutical composition is dosage unit form for treating a condition for which the therapeutic compound is effective, comprising an amount within the range from about 0.1 to about 500 mg of an amino acid transporter compound according to claim 2 per dosage amount therapeutically effective to ameliorate the condition for which the therapeutic compound is effective, together with a pharmaceutically acceptable nontoxic carrier or diluent therefor.

8. A pharmaceutical composition in dosage unit form for treating a condition for which the therapeutic compound is effective, comprising an amount within the range from about 0.1 to about 500 mg of an amino acid transporter compound according to claim 3 per dosage amount therapeutically effective to ameliorate the condition for which the therapeutic compound is effective, together with a pharmaceutically acceptable nontoxic carrier or diluent therefor.

9. A process for treating a condition for which a therapeutic compound is effective, which comprises administering to a warm-blooded animal having the condition a therapeutic and relatively nontoxic amount of amino acid transporter compound according to claim 1, sufficient to ameliorate the condition.

10. A process according to claim 9 in which the amino acid transporter compound is administered in dosage unit form.

11. A process according to claim 9 in which the amino acid transporter compound is administered in an amount with the range from about 0.1 to about 500 mg per day.

12. A process according to claim 9 in which the amino acid transporter compound is administered with an inert diluent or carrier.

13. A process according to claim 9 in which the amino acid transporter compound is administered orally.

14. A process according to claim 9 in which the amino acid transporter compound is administered parenterally.

* * * * *